United States Patent [19]
Bergamini et al.

[11] Patent Number: 4,924,406
[45] Date of Patent: May 8, 1990

[54] OPTICAL SLUB CATCHER, PARTICULARLY SUITABLE FOR OPENEND PROCESS

[75] Inventors: Giorgio Bergamini; Tommaso Cipriani, both of Bari, Italy

[73] Assignee: Nuovopignone Industrie Meccanichee Fonderia S.p.A., Florence, Italy

[21] Appl. No.: 287,516

[22] Filed: Dec. 19, 1988

[30] Foreign Application Priority Data

Oct. 16, 1985 [IT] Italy .............................. 22509 A/85

[51] Int. Cl.⁵ ............................................. G01B 11/00
[52] U.S. Cl. ..................................... 364/470; 28/227; 57/264; 73/160; 242/36; 250/572; 250/563; 340/677; 356/238; 356/385; 356/430
[58] Field of Search ............... 364/552, 470; 356/238, 356/385, 430, 431; 340/677; 250/562, 563, 572; 242/36; 73/160; 57/81, 263, 264; 28/227

[56] References Cited

U.S. PATENT DOCUMENTS

| | | | |
|---|---|---|---|
| 3,887,814 | 6/1975 | Faulhaber | 250/562 |
| 3,930,291 | 1/1976 | Abbot | 242/36 |
| 3,986,037 | 10/1976 | Faulhaber | 250/562 |
| 4,007,457 | 2/1977 | Aeppli | 57/81 |
| 4,045,659 | 8/1977 | Akagawa et al. | 364/470 |
| 4,084,398 | 4/1978 | Stahlecker | 57/264 |
| 4,091,368 | 5/1978 | Schwartz | 250/571 |
| 4,137,699 | 2/1979 | Stahlecker et al. | 57/81 |
| 4,189,841 | 2/1980 | Loepfe | 33/143 L |
| 4,222,224 | 9/1980 | Raasch | 57/81 |
| 4,365,654 | 12/1982 | Viniczay et al. | 340/677 |
| 4,430,720 | 2/1984 | Aemmer | 364/470 |
| 4,436,427 | 3/1984 | Schwartz | 356/238 |
| 4,491,831 | 1/1985 | Sakai et al. | 242/36 |
| 4,553,708 | 11/1985 | Matsui et al. | 242/36 |
| 4,634,280 | 1/1987 | Paulson, Jr. | 356/385 |
| 4,648,054 | 3/1987 | Farah et al. | 73/160 |

Primary Examiner—Allen MacDonald
Attorney, Agent, or Firm—Hedman, Gibson, Costigan & Hoare

[57] ABSTRACT

An optical slub catcher, particularly suitable for openend process weaving machines, comprises a special optical head for the measurement of yarn diameter, the analog signal of which is cleaned of the disturbances due to ambient light. This analog signal is furthermore normalized by an original compensating and normalizing unit, and is then digitized. The slub catcher of the present invention is also provided with the following: a detector unit for the detection of Moire defects, a detector unit for the detection of the % VC irregularities, and a unit for spectrogram processing.

In addition, the slub catcher of the present invention compensates for dirt build-up, thermal drifts, and aging of the optical head which affect the performance of the slub catchers of the prior art.

8 Claims, 5 Drawing Sheets

OPTICAL SLUB CATCHER, PARTICULARLY SUITABLE FOR OPENEND PROCESS

BACKGROUND OF THE INVENTION

The present invention relates to an optical slub catcher which, inter alia, provides uniform lighting of the optical measurement head window as well as efficacious compensation for the soiling, the thermal drift, and the aging of such optical measurement head, and the disturbances created by ambient light. By normalizing signals and by using hybrid digital/analog processing, the present invention, allows, besides the traditional checks on the yarn, also laboratory-typical tests of yarn characteristics with a high degree of precision and stability such as determination of the coefficient of % variation in diameter (also indicated as "% VC", equal to the mean square deviation, as a percentage of the average value of the yarn diameter), the spectrogram or spectral analysis of the irregularities occurring in the yarn, as well as very minor periodical irregularities (Moire) occurring in the yarn. Consequently, the present invention is particularly suitable for application on open-end weaving machines.

From the prior art, various designs of optical slub catchers are known that are suitable for the detection of the yarn defects typical of the coners, such as slubs and/or attenuations of diameter, more or less extended lengthwise. The increasing demand by the weavers for better quality yarns has caused a continuous improvement in weaving techniques, which in the open-end process has resulted in defect levels much lower than those typical of the traditional weaving machines, thus creating a demand for more sensitive slub catchers. On the other side, in the open-end process, further defects, typical of the open-end weaving, occur, which must be detected and eliminated. Among these, the most typical and feared is the so-called Moire, which compromises severely the quality of the yarn, creating local slubs and attenuations in diameter, which occur at constant distance (they are periodical) and which, even if they are of small extent, can give rise to troublesome veins.

Therefore, to detect all of these defects typical of the open-end process, a slub catcher is required that is endowed with characteristics of resolution, precision and stability of the measurements considerably higher than the present standards, such enhanced characteristics basically resulting from a better uniforming of the light throughout the window of the optical detector, by means of an efficient compensation of the thermal disturbances, of the dirt and of the decay, as well as a compensation for the outer lighting. On the other side, the detection of Moire defects requires clearly also the provision of a suitable digital filter which, by allowing the signals to be processed in a digital way, may facilitate not only the detection of Moire, but also the detection of the spectrogram and, above all, the detection of the percent variation coefficient, also defined as "% VC" by the weavers, which characterizes in the most univocal way the real quality, or better described, the irregularity of the yarn.

In the slub catchers of the prior art, various means and contrivances have been used for the purpose of uniforming the measurement light beam throughout the window, such as the bending of the emission and reception plane of the window, the reflection of the light beam on a homogenizing mirror, as well as the correction of the reflection of the mirror by providing lines and reliefs thereon, and the insertion of diffuser filters or grids. But all of these contrivances, however, lead to a decrease in the energy of the light beam, worsening the signal-disturbance ratio, thus giving results which, if can be enough for the slub catchers for coners, are not so for the precision required by the open-end process, above all for the determination of Moire and of the spectrogram.

A second serious drawback of the slub catchers of the prior art is the change in photodiodes emission with temperature.

Also, the photoreceivers suffer from the same type of defect, so that by a proper selection of the components, obtaining a certain degree of compensation is possible, but on the condition that both the elements are at the same temperature.

In the geometrical arrangements of the prior art, however, the receiver and the emitter are always installed on opposite sides, so that, because of their distance during the heating transients following the turning on, or because of an outer irradiation, the two elements can have different temperatures, consequently causing considerable errors.

The extent of such errors can be acceptable for the degree of precision required by the coners, but not at all for the open-end process in which the measurement of Moire requires a higher degree of precision.

As for decreasing or elimination of the outer disturbances caused by the ambient lighting, the prior art has not solved the two problems of the saturation of the amplifiers and the presence of variations in the signal constituting the measure of the diameter, always in the presence of the disturbance created by outer lighting. Both problems result because of the incorrect use of the diode and because of a different dynamic answer of the amplifier circuits when the signals reach very different levels.

According to the present state of the art, no means exist for reducing the phenomenon of saturation but for the installation of filters positioned in front of the receiver, which attenuate all the wave lenghts different from the I.R. band inside which the emitter works.

On the market, no optical slub catcher exists, which is capable of withstanding a light slash due to direct or reflected sun light entering the weaving room.

The collected and amplified signal is always the total signal, so that a gain in the first amplifier stage, optimum for the modulated signal, amplifies obviously also the light, which may reach very high intensity levels. As for the apparent change in yarn diameter in the presence of disturbing light, inasmuch as the disturbing light is of small intensity, the equipment of the prior art has not corrected this problem because it is not critical to the precision typical of the coners.

The equipment of the prior art, completely analog as it relates to the solution of the problem of the compensation for the dirt and of the optical efficiency, both from the viewpoint of the decay and of the thermal disturbances, is provided at most with a type of circuit, wherein all the types of degradation which cause the output to slowly change, are compensated for by just varying the emission so as to keep constant the average output value corresponding to the preset average value of the yarn diameter.

In a typical arrangement, an integrator, with very long time constant, integrates the difference between the signal and the desired average value, and its output is delivered as the emission level set.

The limit of this approach is that the emission is also always varying in the presence of diameter changes of more or less long periodicity and that the compromise involved in executing the calibration of the integration time constant so that a sufficient dynamics of compensation for the dirt be achieved, cannot prevent at the same time what the system may fit in, e.g., a double yarn which is inserted as slowly-varying diameter.

In any case, the detection of the Moire-effect causing defects is only achieved by the prior art when the peaks due to the thickening are so large as to be computated as a chain of knops, i.e., as a not necessarily periodical chain of small slubs.

This approach leads to the possibility of stopping the occurrence of Moire defects only when these are already well evident because detecting the periodicity of the attenuations and of the slubs by using simple systems is not possible.

In the solutions of the prior art, therefore, for the purpose of stopping the occurrence of Moire defects, it is necessary either to impose a very narrow limit to the irregularity of the yarn or to allow a certain irregularity, which can allow already well-evident Moire levels to pass.

Keeping well separate the two measurements is, on the contrary, a weavers' requirement, in that the case could occur when a relatively considerable irregularity is acceptable without renouncing the stopping of just visible Moire levels.

As it has already been anticipated for the Moire, and for the other type of defect, the irregularity of the yarn, the analog means of the prior art carry out a measurement which is only approximately correlated to the most precise definition of the irregularities which is the VC, variation coefficient, mathematically defined by the mean square deviation as a percentage of the average value of diameter.

In the solutions of the prior art, the irregularity is not measured and then possibly compared to a limit, but rather the peaks, i.e., the number of times the measured diameter exceeds a prefixed value, are counted and the stop for excess of irregularity is given when the number of these events exceeds a prefixed value.

This calibration by the prior art is consequently the same for the Moire defect. But even if it allows the occurrence of determined levels of irregularity to be stopped, these levels do not coincide with the % VC level; moreover, when the stop does not occur, a measurement of the actual value of % VC is not available for the accepted yarn.

The spectrogram, or spectral analysis of the irregularities existing in the yarn, is a typical function presently performed by dedicated laboratory equipment, which have such a cost and complexity as to render the spectrogram applicable to yarn samples, but relatively not much representative of the actual quality of the whole production.

The computing of the spectrogram directly on the slub catcher has never been done because the prior art is analog.

Nor does the availability of a microprocessor on each slub catcher automatically solves this problem because the velocity and complexity of the operations, besides the storages required by the computation of Fourier coefficients, are not compatible with the structure and the cost of the microchips available on the market as well as useable for the slub catching control.

SUMMARY OF THE INVENTION

The purpose of the present invention is to obviate the above drawbacks by supplying a novel optical slub catcher which, by exploiting to an optimum extent an 8-bit microchip processor, not only improves and renders more precise the typical performances of the slub catchers, but also concentrates on the same slub catcher all of the functions of electronic supervisory of the weaving unit, presently performed by expensive laboratory equipment, or by ad-hoc installed equipment, which can thus be eliminated. A further advantage is that the high sensitivity of the present system allows not only a Moire defect exceeding a preset threshold level to be detected, but also allows for a forewarning level when the phenomenon is incipient but still acceptable, so as to cause a request for rotor cleaning servicing without the weaving having to be stopped in the meantime, thus maximizing the productivity of the weaving plant.

BRIEF DESCRIPTION OF THE DRAWINGS

The invention is hereunder disclosed with reference to the attached drawings, which show a preferred form of practical embodiment supplied for only exemplifying and not limitative purposes in that technical or structural variants can be practiced within the scope of the present invention.

In said drawings.

Figure 1:
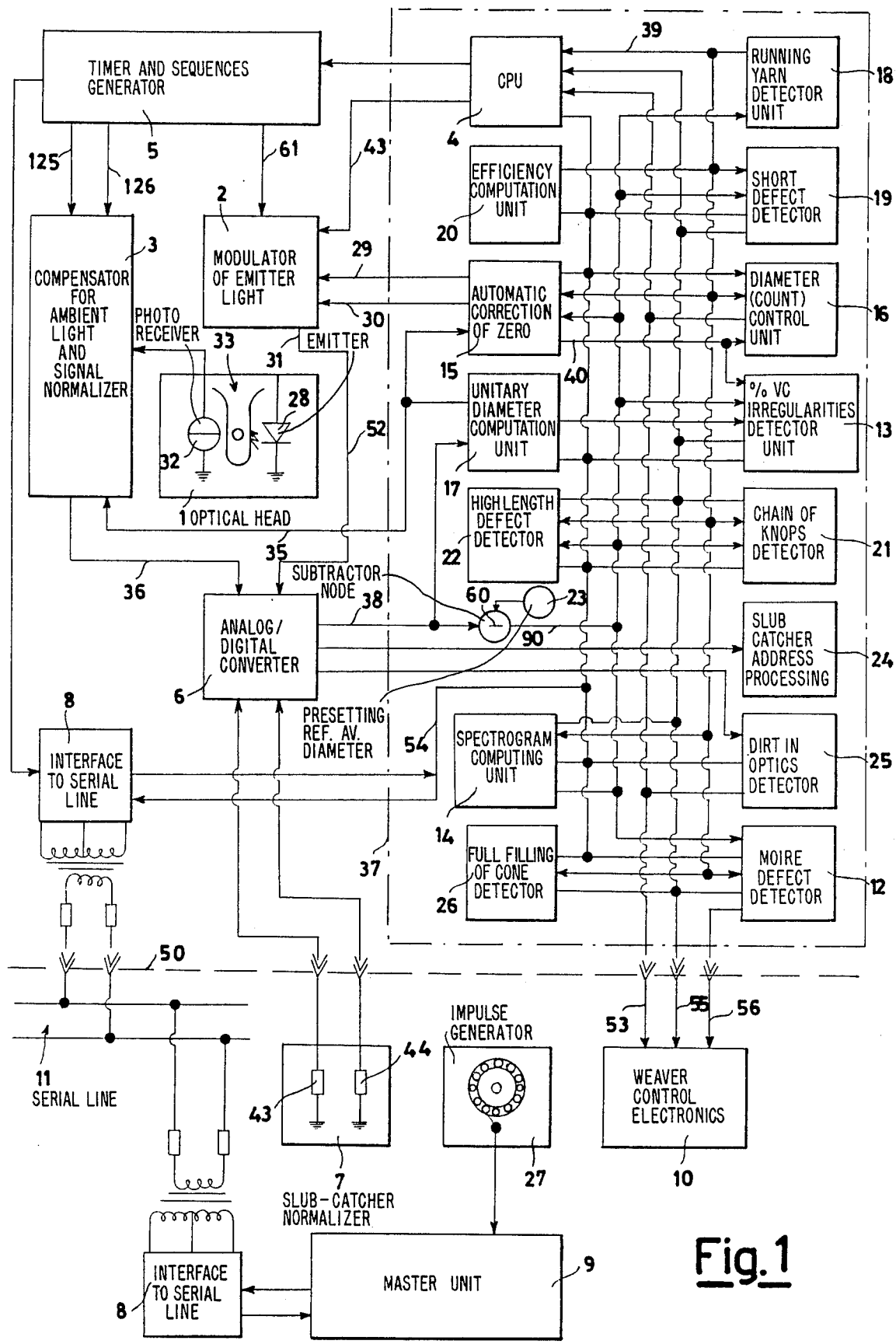
FIG. 1 shows in a block diagram the slub catcher of the present invention, associated to a serial communication line, to which all of the other slub catchers and the master unit, as well as the weaving unit management electronics are connected.

Referring to the figures, and in particular to FIG. 1, the following basic functional blocks are identified:

an optical head 1 for the measurement of the yarn diameter;

a unit for the modulation of the emitter light, provided with digital analog converter, 2;

a unit for the compensation of the disturbances by the ambient light and signal normalization, 3;

a data processing unit CPU (Central Process Unit) 4;
a timer and sequences generator, 5;
an analog/digital converter, 6;
a slub-catcher normalizer block, with resistors, 7;
an interface unit to the serial line, 8;
a MASTER unit 9;
the weaving unit control electronics 10;
a serial line 11 for the connection to the other slub catchers to the MASTER unit;
a Moire defects detector unit 12;
a % VC-irregularities detector unit, 13;
a spectrogram computing unit, 14;
a unit for the automatic correction of the zero, 15;
a diameter (count) control unit 16;
a unitary diameter computation unit, 17;
a running yarn detector unit 18;
a unit for the detection of the individual defects of a certain extent (short defects), 19;
an efficiency computation unit 20;
a unit for detecting the chain of knops, i.e., of the small aperiodic slubs, 21;
a unit for the detection of high-length defects, 22;
a unit for presetting the reference average diameter $D_m$, 23;
a slub catcher address processing unit 24;
a unit for detecting the excess of dirt in the optics of the head, 25;
a unit for the detection of the full filling of the cone to the preset yarn length, 26;
an impulse generator 27 keyed onto the yarn extractor roller;
a subtractor node 60.

DETAILED DESCRIPTION OF THE PREFERRED EMBODIMENT

The slub catcher of the present invention operates as follows:

A unit 2 for the modulation of the light from the emitter 28 of the optical head 1 supplies said emitted with a pulsating current, with lighting on and lighting off periods equal (but they could also be different from each other), and driven by the sequences-generator timer 5.

The emission current 31 is adjusted at a level determined by the automatic zero correction unit 15.

Said unit 15 is connected to the modulator unit by two channels 29 and 30, which transmit sets of impulses respectively as follows: the channel 29 to increase and the channel 30 to decrease the emission level 31 of the emitter diode.

The emitted light is delivered to the photoreceiver 32, through a detection window 33, inside which the yarn in question 34 runs.

The amount of light received by the receiver 32 decreases linearly with the increasing of the diameter of yarn 34, up to the greatest diameter compatible with the size of window 33.

The photoreceiver 32 is made to operate as a current generator, so that the current generated is proportional to the light received and hence the current variations result is proportional to the diameter of the yarn in question.

The signal supplied by the photoreceiver is amplified and demodulated by the related circuit 3, which also performs the normalization of this signal by means of a variable-gain amplifier digitally controlled, through the connection 35, by the unitary diameter computation unit 17.

The analog signal normalized, and hence constant with varying diameter of the yarn to be processed by the slub catcher, is conveyed, through the connection 36, to the 8-bit digital analog converter 6, which converts it into an 8-bit digital value, i.e., into a number ranging from 0 to 256, with a sampling cadence or period corresponding to a prefixed yarn length, e.g., 2.5 mm.

The number corresponding to the diameter measured is delivered, by the connection 38, to the microprocessor 37, respectively to the subtractor node 60 and to the unitary diameter computation unit 17.

In the first step of operation of the slub catcher, when the rated diameter is detected, in the same unit 17 an average is calculated of the values read on a prefixed yarn length comprised within the range of from 64 to 256 meters of yarn.

In this step, to the variable-gain amplifier of unit 3, by the unit 17 a particular configuration, close to the highest gain, is given, such that the number corresponding to the average of the detected values, besides representing in digital form the average unitary diameter, constitutes also, in its configuration of binary digit, the normalization gain to give to unit 3, for the purpose of obtaining normalized values with that particular yarn.

The average diameter computated in 17 is delivered, through the serial line interface 8, to master 9.

Master 9, after receiving the average diameter values from all of the slub catchers enabled to perform this operation, calculates the average value thereof, and returns this value back to all of the slub catchers, in which it is used as a control, through unit 17, to drive the configuration of the variable-gain amplifier of unit 3.

After determination of the average diameter, the slub catching starts, which operates always by starting from the difference of the measured diameter, carried out in the subtractor node 60, relative to a value, 23, which represents the reference average value.

Said difference, which represents, by means of a digit with sign "+" or sign "−", the error relative to the reference diameter, is reported, by the wire 90, to the various functional units for detection of the defects and to the service units required by the operation of the system.

Starting from the service units, the first one of these, 18, carries out the detection of the running yarn.

In this unit, 18, repeated equal values of said differences cause the emission of a signal of "stationary" or "absent" yarn, while the variability of said differences on a plurality of samples, of greater value than the uncertainties of the converter, 6, determines the signal of "running" yarn.

The "running" yarn signal enables, through the connection 39, all the slub catching functions and also the yarn length calculating unit 26.

The signal of "stationary" yarn is used to enable the count of the time of inoperative status in unit 20, which processes the data of efficiency of the weaving unit.

The second service unit, 15, carries out the correction of the zero following such disturbances as presence of dirt in optical unit 1, the thermal drift of emitter 28 and of receiver 32, and the thermal drift of the circuits of adjustment of emission 2 and of the demodulator amplifier of unit 3.

The operating mechanism is as follows:

In unit 15 a summation is carried out, extended to a length of yarn of from 16 to 32 meters, of the said differences representing the deviation from the reference diameter.

In such a long yarn length, the value of the average of the above said differences should be zero, inasmuch as all the irregularities generally have a much smaller length, and as it is assumed that the weaving units feed sliver has a very constant count.

Should it not be so, deviations of relatively small values corresponding to a few % of the average value of said deviations are attributable to instrument type error, caused by the above mentioned disturbances.

The correction of said zero error is automatically carried out, at the integration end, by the unit 15, which increases, by means of connections 20 and 30, or reduces, the emission level of photoemitter 28, through the circuit 2.

To achieve this outcome, the result from the integrations of said deviations on 16–32 meters is multiplied times the inverse of the gain of normalization of signal generated by the unit 17 and supplied for that purpose to unit 15, through the connection 35, and the obtained number is converted into impulses to increase or to decrease the emission level.

The resolution and precision of the system allow an exact recovery of the error found, by a hence automatic recalibration of the zero.

The digital integration on a great length of yarn prevents that possible fluctuations in diameter, even of medium length, may be considered as zeo errors, and hence that unsuitable and dangerous corrections may be made to the zero calibration.

In this regard, above a certain percent value of the said average of the deviations, the correction is no longer increased, and the value of said average is furthermore supplied, via connection 40, to the count control unit 16, wherein it is compared to a limit which is defined as the maximum allowed count deviation; if it exceeds said value, from unit 16 a signal of weave-stopping is generated, and supplied, via connection 42, to the weaving unit control electronics 10, causing the call to the operator, i.e., the alarm.

The sophistication of the operations described, and in particular the use of the digital average and the periodical and non-continuous updating of the zero are designed to keep remote such a drawback, typical of the slub catching systems with automatic zero recalibration, as the learning of a wrong count.

In the disclosed system, such an event could occur only in the very unlikely case that the variation in diameter be gradual and equal to a few % every 16–32 meters of yarn.

At each sampling, the value of the deviation from the average diameter is then supplied to unit 12 which processes the control of the Moire-generating defects; following these processings, the generated signal can be either a forewarning signal or a weave-stopping signal which is sent to the electronics of management of the weaving unit 10, through connections 56 and 55 respectively. Another unit 19 processes, on the basis of the sampled values of the deviations from the average diameter, the control of the individual defects of a certain magnitude. The result of the processing is a further stop signal, if the defects exceed the limits.

A further unit 21 controls, always by starting from the sampled values of the deviations from the average diameter, the small aperiodic slubs, also named "chains of knops," with the possible generation of a stop signal.

Thereafter, in unit 13 the means square deviation is computated of the sampled values of the deviations from the average diameter, which represents the degree of yarn irregularity, defined by the weavers as "% VC", "% variation coefficient".

Also this unit can generate a stop signal due to an excess of irregularities.

Another functional unit, 14, processes the spectrogram and can also generate a stop signal if the highest amplitude level of the Fourier coefficient, at any wave length, exceeds a presettable value. Exceeding the present value of the spectrum level is an indication of excessive irregularity and also of a Moire-type defect of a certain magnitude.

At the end, some ancillary or optional functions are performed by other units, starting from the signal produced by the above mentioned electronic circuitry.

The first one of these units, 24, provides the processing of the address of the slub catcher by starting from the detection of the values of two resistors, 44 and 45, contained in a so-called "slub-catcher-personalizing resistor-type block", 7, which is housed in the stationary portion of the power supply and connection connector, 50, to the serial line 11 of interconnection of the slub catcher to the master 9.

Said values are read and, after being converted into numbers by the analog-digital converter 6, are transferred to the unit 25 which, by using only 4 bits, the most meaningful of each one of the two numbers, composes the 8-bit address of the slub catcher (thus, 256 addresses are possible).

A second unit 25 provides the detection of the degree of dirt and decay in the optics of the head 1.

Said detection is obtained from the measurement of the emission level reached by the circuit 2, which is sent to the analog-digital converter 6 through the connection 52. The operating principle is based on the fact that, the more the dirt, the more the emission has to be increased, so that a maximum level preset of the emission is used by the unit 25 as a limit value for the request for cleaning by the operator (alarm).

The alarm signal generated by the said unit 25 is delivered to the electronics of management of the weaving unit 10 through wire 53 and through wire 54 to the interfacing unit 8 to the master 9.

Another unit, 20, accomplishes the computation of the efficiency of the weaving unit by starting from the addition of the inoperative times of the weaving unit.

The sum of the inoperative times due to a stop, communicated to the weaving unit 10 management electronics via the connection 55, where the stop is followed by the automatic actuation of the robot car that cleans the open-end rotor and rejoins the yarn, is formed separately from the sum of the stops which are caused by an alarm to the operator for all of those servicings which cannot be performed automatically.

This data, communicated to the master 9, through the interface unit to the serial line 8, allow the car efficiency, the operator efficiency and the overall efficiency to be calculated.

At the end, the unit computing the yarn length, 26, is preset by the master, at a number of meters corresponding to the full filling of the cone; after the resetting consequent to the unloading of the full cone, the samplings, which correspond to well precise unitary lengths of the running yarn, are counted, until the number corresponding to the cone filling is reached.

At this point, the signal of "cone unloading" is generated.

Figure 2:
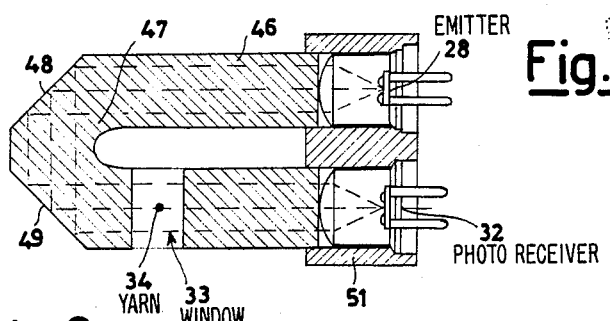
FIG. 2 shows a top sectional view of the optical measurement head of the slub catcher of FIG. 1.

Then according to a preferred form of practical embodiment of the present invention, the said optical measurement head 1 is constituted by a block of plastic or glass 46 (see specifically FIG. 2), substantially "U"-shaped, which acts as a guide for the light beam 47 emitted by a photoemitter 28 provided at an end of a prong of the said "U". Said light beam 47 is reflected twice on the two smooth reflecting surfaces 48 and 49, surfaces inclined by 45°. After passing through the optical window 33 of detection of the yarn 34, light beam 47 consequently has a varying intensity which is inversely proportionally to the diameter of said yarn. Light beam 47 then comes to a photoreceiver 32, positioned at the end of the other prong of the "U," which is embedded together with the photoemitter 28 in a block 51 of a material able to keep equal the temperature of the two elements.

Such an embodiment solves in an efficacious way the two main problems characteristic of this type of component: the linearity and homogeneousness of lighting of the measurement window 33 through which the yarn 34 passes and the minimization of the disturbances caused by a difference in temperature between the emitter 28 and the receiver 32.

In fact, the double reflection allows an optimum effect of mixing of the light rays, and hence the homogenizing of the light beam to be achieved. Such homogenizing is also enhanced by the long optical path, which serves to reinforce the light beam in correspondence of the edges where the emission is weaker, by means of the reflections of the rays against the walls of block 46.

Said homogenizing furthermore does not go to the detriment of the efficiency of the system because it does not involve losses in light energy.

Furthermore, having the emitter 28 and the receiver 32 very close to each other causes them to always have the same temperature; the block 51 guarantees that a change in temperature acts on both elements 28 and 32 in the same way.

Figure 3:
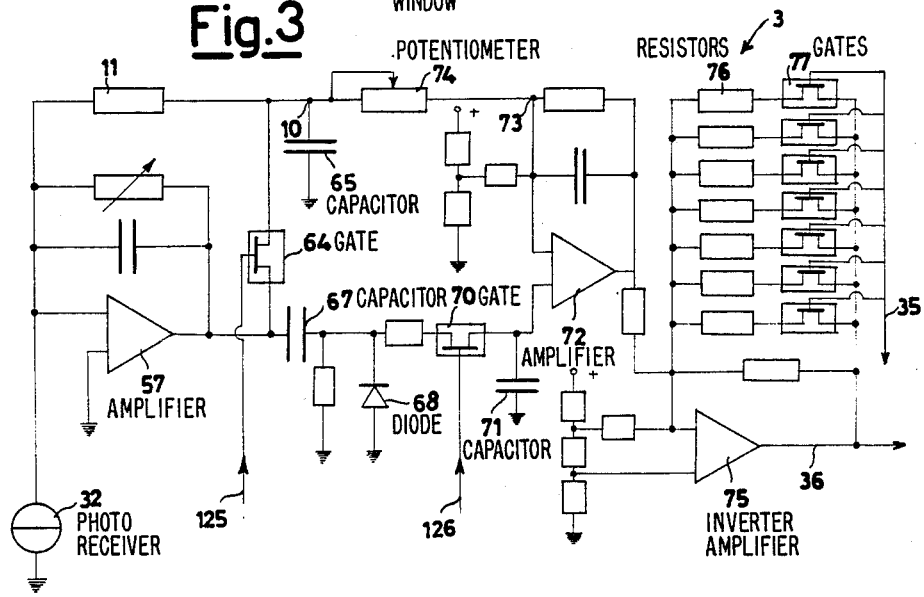
FIG. 3 shows the circuit diagram of the unit for the compensation for the disturbances by the ambient light and for the signal normalization of the slub catcher of FIG. 1.

Then, according to a further characteristic of the instant invention, the unit 3 of compensation for ambient light disturbances and signal normalizing (see FIG. 3) provides the demodulation of the signal emitted by the receiver photodiode 32, which is connected through the circuitry to the amplifier 57, so as to operate a pure, i.e., short-circuited current generator for the purpose of obtaining the highest linearity between received light and current.

Figure 4:
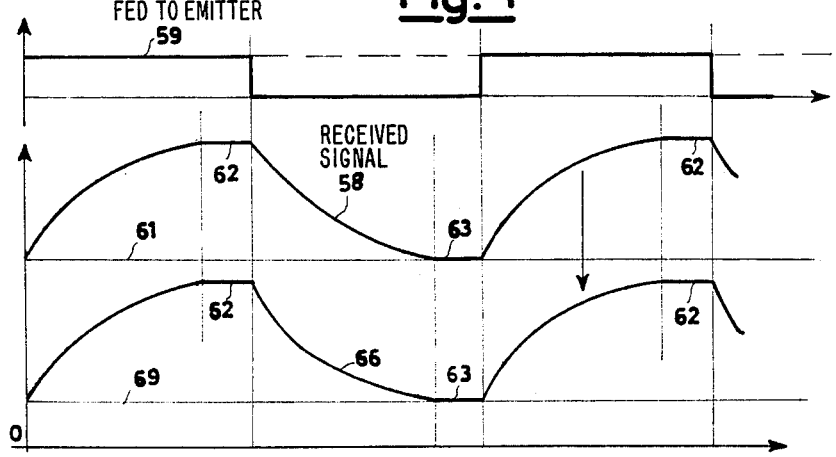
FIG. 4 shows a chart relating to the operation of the compensation unit of FIG. 3.

The trend of the received signal is shown in FIG. 4 and is indicated by the curve 58.

In the same FIG. 4, the broken line 59, representing the pulsation law of the current which is fed to the emitter photodiode 28 is also shown.

In the photoemitter 28, the emission sinks periodically to zero while the photoreceiver 32 supplies a signal that is higher than zero at its minimum values, level 61. The photoreceiver's signal is higher than zero at its minimum values because of the ambient light, which gives a disturbance raising to a considerable extent, the signal's continuous component level. To prevent the amplifier 57 from being saturated by this type of disturbance, a reduction system for said continuous signal has been provided according to the present invention. In the present invention, said reduction takes place without decreasing the dynamic characteristics of the signal by essentially subtracting from the value of the signal, represented by the curve 58 with peak points 62, the value of minimum 63.

Said system consists in sampling, through the gate 64 and the capacitor 65, the signal 58 in its points of minimum 63, on command by the timer and frequency generator 5 acting on the gate 64 through the wire 125.

This signal is delivered at a constant level 61 in positive feedback to the amplifier 57, with the resulting shift downwards (see FIG. 4) to curve 66, the signal from the amplifier 57, avoiding saturation.

Through the capacitor 67, the signal, completely liberated of the residual continuous component 69, is entirely raised by the diode 68 above the zero so that the system constituted by the gate 70 and the capacitor 71 may sample signals always having a value higher than zero.

Said sampler, always on command by the timer and frequency generator 5 acting through the connection 126, collects the signal at its highest level 62. The amplifier 72 potentiates the signal by means of circuitry characteristic of the present invention, thus correcting a typical error of said signal caused by the ambient light disturbance.

Said error occurs systematically as an apparent non-linearity of the photoreceiver diode 32, but is actually due to the dynamics of circuital processing of the signal. The error involves an increase of the modulation and of the signal, corresponding to a decrease in the detected yarn diameter, when the intensity of the ambient light disturbance increases. The elimination of this error has been obtained by adding to the input to amplifier 72, in node 73, a fraction of the voltage sampled in capacitor 65, and which represents a fraction of the level of the ambient light disturbance, according to the calibration of the potentiometer 74.

The optimum value of this calibration is obtained by submitting the slub catcher to different levels of disturbing lighting and minimizing, by means of corrections to the potentiator unit 74, the variations in the output from amplifier 72.

Said output from amplifier 72 is delivered (see FIG. 3) to a further inverter amplifier 75, provided with resistors 76 suitable to be connected in parallel to the feedback, so to increase the gain thereof.

Said resistors 76 are inserted by means of the gates 77 and are commanded in their turn by the unit 17, through the connection 35, which can hence represent, in digital form, the gain of said amplifier 75 according to the combination of inserted resistors.

According to a characteristic of the present invention, the values of said resistors 76 are related to one another by the doubling law, thus accomplishing a series of powers of two, with the result that the inverse of the gain of this amplifier is linearly proportional to the binary number corresponding to the configuration of inserted resistors. The amplifier 75, with this characteristic, renders the signal emitted by said amplifier, which represents the measured yarn diameter, constant relative to the preset unitary diameter because it carries out, actually, the division of the input signal by a number proportional to the calibration unitary diameter.

Hence, by presetting said resistors 76 according to a number porportional to the unitary calibration diameter of the slub catcher, a signal is obtained that always represents the % value of the measured diameter relative to the calibration diameter-hence a normalized signal.

According to a further characteristic of the present invention, the reference voltage of said amplifier 75 is set at a value higher than zero so that the output signal, when the zeroing occurs of the measured diameter (corresponding to the absence of yarn), is not zero.

Therefore, under this signal of zero, also called "living zero," the signal represents negative diameters, the physical meaning of which can only be a circuit miscalibration, which can be detected in this way.

Said signal is delivered, through the connecton 36, to the analog-digital converter 6, which periodically converts the signal into a number which always takes either of two precise values because of said normalization. These two values correspond to a lack of yarn and to when a yarn is inserted, which has a diameter exactly equal to the unitary calibration diameter. In the subtractor node 60, from the input signal, a fixed value 23 is subtracted, the fixed value 23 being equal to the said number corresponding to the unitary diameter, so that at the output from said node a sampled value of the deviation of the measured diameter from said unitary diameter is available.

According to still a further characteristic of this invention, a unit of automatic correction of the zero value 15 provides the correction of the zero calibration, so as to cause the said deviation to become referrable to the average yarn diameter.

Figure 5:
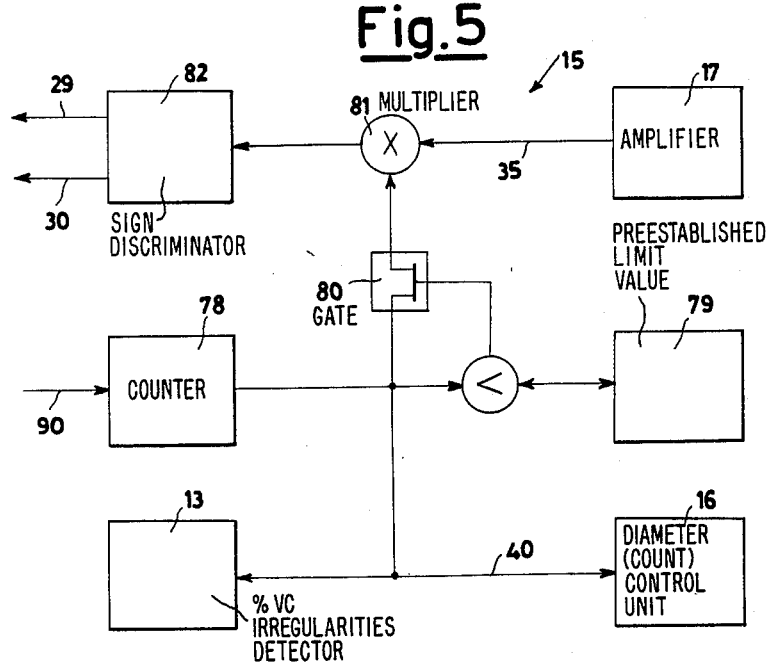
FIG. 5 shows the circuit diagram of the automatic zero correction unit of the slub catcher of FIG. 1.

In the circuit diagram of FIG. 5, the processing is shown of the signals from the said unit for the automatic correction of the zero value. The sampled value of the said deviation and the value of the inverse of the gain preset in the amplifier 75 constitute the input; two signals, the one, 29, to increase and the other, 30, to decrease the current level of the emitter 28 of the optical head 1, constitute the output.

The correction of the zero takes place through the correction of the level of light emission.

This correction is made necessary by the possibility of accumulation of dirt in the optical window 33 of the measurement head, by the aging of the plastic material conducting the emitted light, by the decay and the thermal drifts of the emitter 28 and of the receiver 32, as well as the thermal drifts of the circuits contained in the unit for the compensation of the ambient light disturbances 3 and in the unit for the modulation of the light of the emitter 2.

The mechanism of the automatic calibration of the zero is based on the zeroing, by an action of the type of an integral, of the input signal to unit 15.

It is a characteristic of the present invention that the integration is carried out digitally on the sampled values of the deviations by means of the counter 78, for a number of samples equivalent to a very long yarn length (e.g., 16–32 meters), so as not to be influenced by the final value obtained, which represents the average of the deviations arising from of the small-length and medium-length variations in diameter. Moreover, in the emission no corrections consequent to said integration are supplied. But said integration is complete only following a check having the purpose of ensuring that the correction of the zero does not prevent the detection of an actual variation in the average diameter due to a count error.

To that purpose, the result of the additions carried out by the counter 78 is compared to a preestablished limit 79 and only in the case that the said limit is not exceeded is the transfer of the value of the average deviation enabled through gate 80 to the multiplier 81, wherein it is multiplied times the inverse of the gain of amplifier 75.

The above said limit serves to differentiate the small deviations of the average of the sampled deviations resulting from the above said disturbances, such as the dirt, from those to be ascribed on the contrary to count errors.

Only in the case of the first type of deviations, is the correction carried out, which is precisely obtained, in order to obtain the exact zeroing of said deviation. Such correction is obtained by multiplying the average deviation times the inverse of the gain of amplifier 17, in order to render said correction absolute, by starting from a deviation value which is, on the contrary, normalized.

The numeric value of the result of said multiplication is converted by the sign discriminator 82 into a set of impulses on two channels, 29 and 30, as a function of the sign of said average of the deviations.

Said average of the deviations is also sent, through the connection 40, to the diameter (count) control unit 16, wherein it is compared to an operator-calibratable limit value, to produce an alarm signal deriving from an error in the count, and to the unit for the detection of the % VC irregularities 13, wherein it is used for the purpose of rendering more exact the computation of the variation coefficient, % VC.

Figure 6:
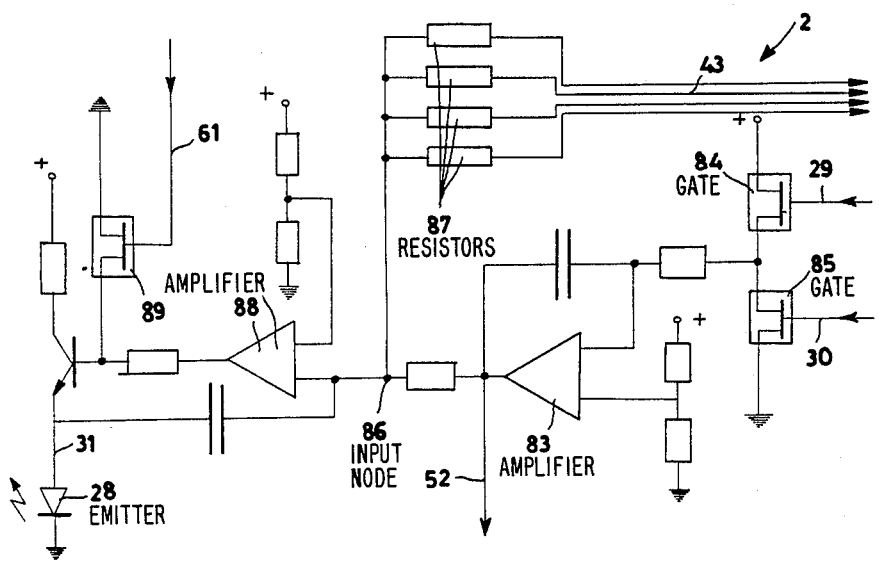
FIG. 6 shows the circuit diagram of the photodiode emission modulation unit with digital-analog converter, of the slub catcher of FIG. 1.

According to a further characteristic of the instant invention, a photodiode emission modulator unit 2 with digital-analog converter converts the said set of impulses into an analog level of voltage, to which a determined level of the current delivered to the emitted 28, corresponds (see FIG. 6). The function of digital-analog converter is performed by the integrator circuit leading to the amplifier 83, with an increase or a decrease in the output level, respectively caused by the gate 84 and by the gate 85, driven by the channels 29 and 30, and the central point of which is connected to the above said integrator. The integrator has its own reference anchored to an intermediate voltage between the voltages applied to gates 84 and 85.

The high resolution accomplished by this converter is made necessary by the large variability of the number of impulses computated by the units 15, to obtain an exact recovery of the error of the zero.

The result of this conversion is delivered, by means of the connection 52, to the analog-digital converter 6 for the purpose of monitoring, according to a characteristic of the present invention, a possible excess on the optics 1 of dirt. The dirt is detected by unit 25 which detects an excess of dirt on the head optics. The detection of such excess dirt generates an alarm signal requesting servicing by the operator.

According to a characteristic of the present invention, to expand the intervention range of the said digital-analog converter to catch very high dirt levels, on the the input node 86 to the amplifier 88, which regulates the current delivered to the photoemitter 28, a set of resistors 87 have been connected. This set of resistors 87 are connected to as many logic outputs of the data processing unit C.P.U. 4 as recommended, allowing the emission current regulation signal to be shifted upwards as a function of how many thereof have been inserted.

Finally, by the sequential turning on and off of the photoemitter diode 28, driven by the unit 5 through the connection 61 and the gate 89, that modulation of the light is attained which allows the effects of the ambient light disturbance to be eliminated by the circuit 3.

Figure 7:
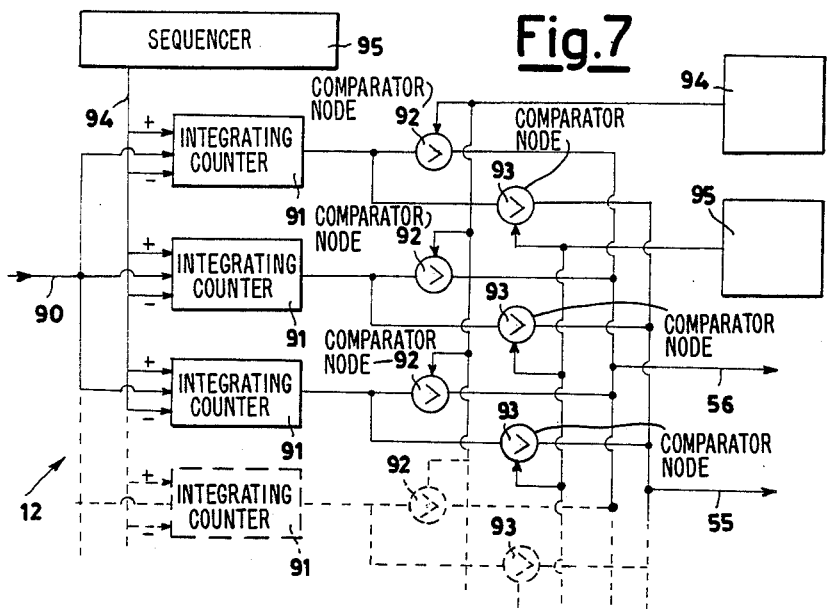
FIG. 7 shows a functional diagram of the unit for the detection of Moire defects of the slub catcher of FIG. 1.

According to another characteristic of the present invention, the unit for the detection of the Moire defects 12 is represented by the block diagram of FIG. 7.

In unit 12, the input is constituted by the sampled deviations values from the average diameter obtained from connection 90.

Said sampled values are added or subtracted in a certain number of integrating counters 91 according to a sequence, driven through the connections 94 of the sequencer 95, which periodically provides, first the subtracting of Z sequential sampled values, and then the sum of further Z subsequent sampled values. Then there is the wait, without performing operations, for such a number of samplings as start again the subtraction cycle, after the passage of a yarn length corresponding to one rotor revolution, i.e., equal to, but not necessarily, to the development of the inner diameter of the same rotor.

For each integrator 91, the sequence starts out of phase relative to the prior sequence of Z samples. The number of said intergrators is determined on the basis of the number of samples Z per step and of the development of the diamter of the rotor, in order not to lose any sampling and hence to control the whole yarn length.

Said sequence is repeated for a yarn length corresponding to some meters.

At the end of said sequence, the output from each counter is delivered to two comparator nodes, 92 and 93, wherein it is respectively compared to a Moire forewarning threshold value corresponding to an unacceptable level of Moire defects, 95.

In case either of these threshold limits is exceeded, a Moire forewarning signal is respectively generated along the connection 56 or a machine stop signal is generated along the connection 55, the signal being sent to the electronics of management of weaving unit 10.

The function performed by the said circuit of FIG. allows said circuit to be defined as a "digital filter", which arises from the discretization of the equation for the calculation of the Fourier coefficients.

Figure 8:
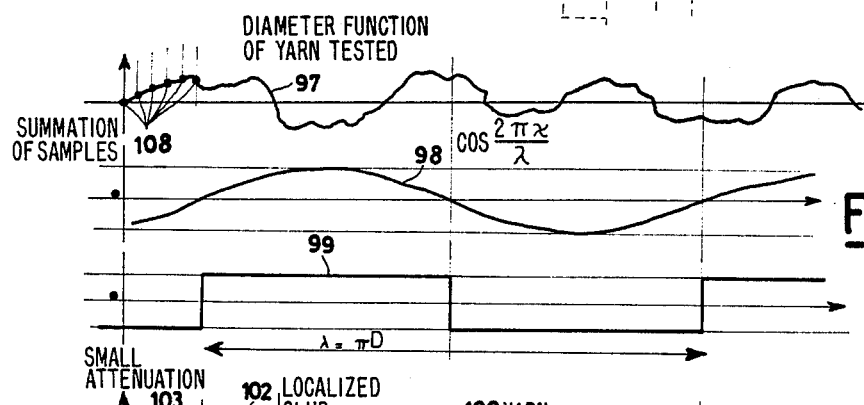
FIGS. 8 and 9 show charts relating to the operation of the unit of FIG. 7.

The Fourier coefficient equation is as follows:

$$a_\lambda = \frac{1}{n\lambda} \int_0^{n\lambda} f(x) \cdot \cos \frac{2\pi x}{\lambda} dx \qquad (I)$$

wherein $\lambda$ is a known wavelength, the content, as amplitude, of which in a signal f(x), such as the curve 97 in FIG. 8, which represents the "diameter" function of the yarn tested, is searched as coefficient $a_\lambda$. Coefficient $a_\lambda$ can be computated with results approximate, but sufficient to the purpose of the present equipment, by discretizing the equation (I), i.e., by assigning to the integration differentials, dx, finished values $\Delta x$ which, in our case, are made equal to $\lambda/2$.

In this way (see FIG. 8), the term:

$$\cos \frac{2\pi x}{\lambda},$$

curve 98, can assume the values "−1" or "+1"; the integral, in case the function f(x) is a sampling function per each length of yarn equal to $$\frac{\lambda}{2Z}$$

becomes the summation of the said samples 108, with sign "−" or sign "+" (broken line 99), calculated every $\lambda/Z$ yarn lengths, or Z samples.

The discretized computation equation thus assumes, according to a characteristic of the present invention, the following form:

$$a_\lambda = \frac{1}{2nZ} \sum_1^{2nz} \pm f(x) \qquad (II)$$

Figure 9:
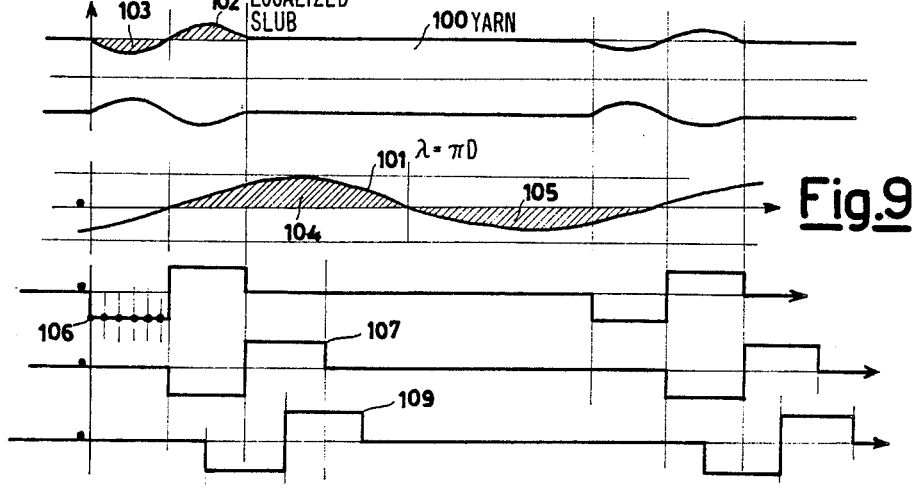

As seen in FIG. 9, in the formation of the Moire defect, the presence of a clot of dirt in the rotor of open-end causes a small attenuation 103 in the yarn 100, then a localized slub 102, the harmonic content of which, curve 101, referred to a wavelength $\lambda = \pi D$, wherein D is the diameter of the rotor of the open-end, is very small; it is evidenced by the small value of the ratio between the areas, corresponding to the sections of the above said sections 102 and 103, relative to the areas, 104 and 105. According to a characteristic of the present invention, in order to attain the detection, the contrivance has been used of carrying out the integration of the signals by small periods, broken line 106, corresponding to 2Z samples, the integration being interrupted for a certain time period, and it being restarted with periodicity, the whole being repeated n times.

If the defect occurs perfectly in phase with this filter, and the number n is high enough, typically 16 times, the result is a very high sensitivity that is capable of detecting defects in their incipient stage.

An object of the present invention is also the method for solving the problem of the phase. By operating in digital mode, a plurality of integrators are made to operate in parallel, all of them being out of phase relative to each other by Z′ sampling periods, up to cover the whole wavelength $\lambda = \pi D$.

Each one of these integrators performs the operation of formula (II), and the one which gives the highest result defines (a) that that one is the integrator in phase, and (b) that the result obtained represents the amplitude, approximate, of the defect.

The result $a_{\lambda max}$ found is compared to two threshold values which represent: the higher being the unacceptable Moire level requiring weaving stopping; and the lower being a Moire level which is acceptable, but which is already detectable. At this lower threshold value, weaving is possible, but the cleaning of the rotor is required at the first traverse of the unit intended for that purpose.

The existence of this second threshold, denominated "Moire forewarning," and the whole method developed to achieve results precise enough to justify it are a characteristic of the present invention.

A better approximation of the amplitude of the defect would require the method claimed in the unit for the detection of the spectrogram 14. This method consists of operating a second integrator associated to each one of the already mentioned integrators, out of phase of Z′/2 samplings (see wave 109 of FIG. 9), and of calculating the term $$\sqrt{a_\lambda^2 + b_\lambda^2}$$

corresponding to the modulus of the two coefficients $a_\lambda$ and $b_\lambda$. These two coefficients are obtained from the two integrators which perform samplings out of phase by 90° and hence relating to the sinus and cosinus according to Fourier, and which would yield the exact amplitude of the defect independently from its phase relatively to that of the integrators.

For the Moire defect, this procedure is not necessary because small phase shifts, between the theoretical sampling period $\pi D$ and the actual yarn sliding, fulfill the task of rapidly bringing in phase one of the integrators, and hence of detecting the possible Moire signal.

As regards the detection fastness, inasmuch as the sampling periods are, e.g., 16 and the value $\pi D$ is, e.g., around 0.2 m, for this system to detect the Moire value, the inspection is sufficient of, e.g., 3.2 m of yarn ($\pm$ as a function of $\pi D$, which can vary, e.g., within the range of from 0.1 m to 0.3 m) or slightly more, if the signal is not in phase. The prior art, however, which does not use a digital filter derived from Fourier, provides, in order to detect very high Moire levels, the analysis of from 30 to 50 meters of yarn (one order of magnitude more than the present invention).

This characteristic is important for the present invention because it involves a theoretical efficiency of the plant better than that obtainable by using the slub catchers of the prior art.

The difference consists in this: by the present invention, after the Moire-caused stop, only a few meters of yarn are wound on the cone, which can then be removed during the normal operation of automatic rotor cleaning without any servicing by the operator.

By the slub catchers of the prior art, however, after the stop, an amount of yarn wound on the cone exists, 30–100 m, and which cannot be removed automatically except by the operator only.

All the types of defects, which cannot be removed in an automatic fashion, increase the servicing by the operator, thus leading to a reduction in the number of the weaving heads per operator or, in any case, to a lower productivity per operator wait.

Figure 10:
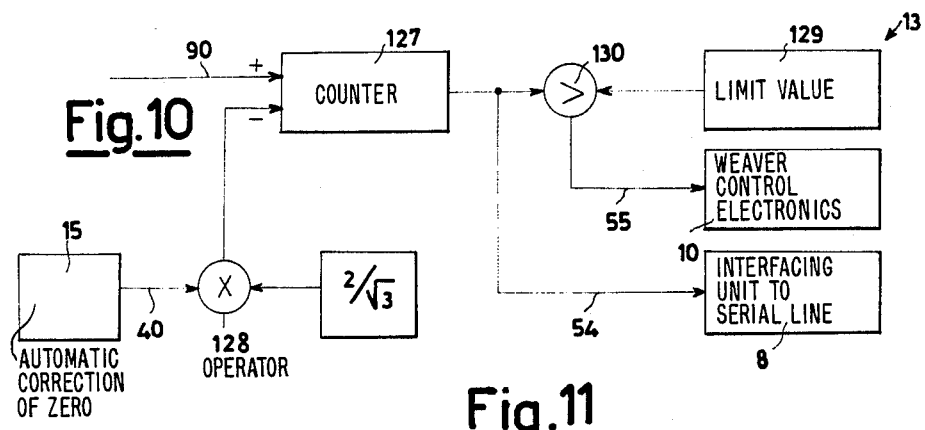
FIG. 10 shows the circuit diagram of the unit for the detection of the irregularities of the percent variation coefficient % VC.

According to another characteristic of the present invention, a unit 10, which provides the detection of the irregularity in the form of a coefficient of % variation, % VC, is composed by the circuit blocks as disclosed by FIG. 10.

A counter 127, with raising to the second power of the input values; receives two signals, one of which is constituted by the values of the deviations from the average diameter, coming from the subtractor node 60 along the connection 90; the other one, which is subtracted, is constituted by the average of the values of the same deviations as computed by the unit for the automatic correction of the zero 15, received through the connection 40, and multiplied by the operator 128 times the reduction factor of $2/\sqrt{3}$.

The operation of sum formation is extended for a number of samples corresponding to 150 meters of yarn after which the result from the said counter 127 is compared, 130, to a maximum level limit of acceptable % VC, which produces when exceeded a stop signal due to % VC excess, communicated by the connection 55 to the electronics of management of the weaving unit 10. However, said output value is delivered along the connection 55 to the master unit 9, by means of the interfacing unit to the serial line 8.

As regards the operations previously described, the algorithm selected by the illustrated diagram is of the theoretical formula:

$$\% \, VC = \sqrt{\Sigma \, e_D^2}$$

corresponding to the computation of the average mean deviation.

In the counter 127, to each sampling, the value of the deviation raised to the second power is added, for a total of samples corresponding to 150 meters.

At the end, a total is available, of which the square root is not extracted, because calculating the second power of the limit value 129 multiplied times the number of the sample is equivalent and less burdensome for the purpose of rendering comparable the two numbers.

On the contrary, in the Master unit which has high computation capacities, the data is normalized and the square root extracted, for the purpose of displaying the theoretical data as the percentage of the variation coefficient (% VC) and of accomplishing the average values on the whole production.

According to a characteristic of the present invention, the circuit which subtracts a fraction, equal to the $2/\sqrt{3}$ of the value of the average deviation on a determined length and processed by the unit for the automatic correction of the zero 15, allows making more precise the calculation of % VC.

During the operation of the slub catcher, the values of the gauges can be afflicted by a small error due to the dirt, to the thermal drift, etc., which, at each determined yarn length, is recovered by the average diameter tracking circuit through correction of the emission.

Said error can distort the computation of the % VC. The above said additional circuit eliminates this error with exactness in the hypothesis that the shift of the zero is linear with time while the multiplying factor $2/\sqrt{3}$ renders homogeneous (according to an obvious mathematical relationship, the justification of which is omitted) the integrated values of the average of the deviations, with the average of the squares of said deviations, from which said integrated values are subtracted, after a preliminary raising to the second power.

Figure 11:
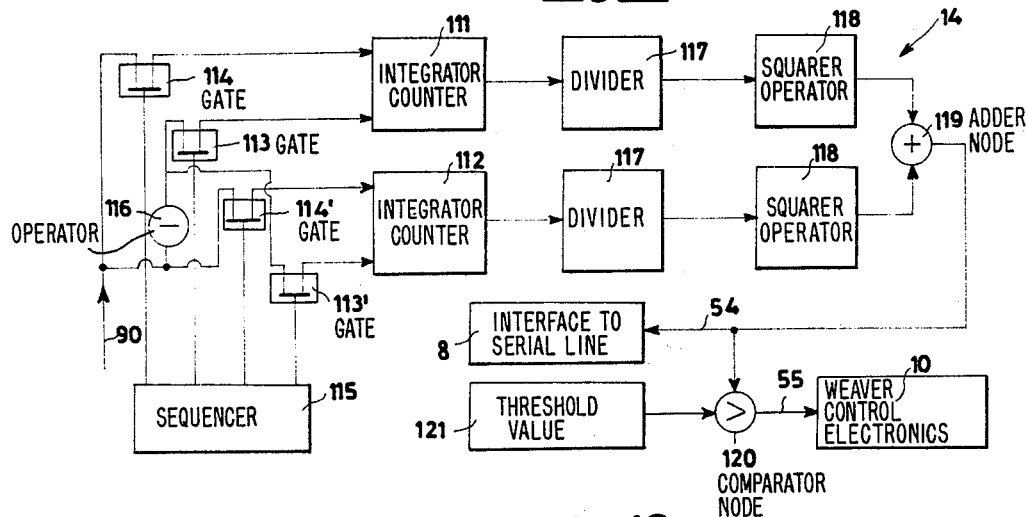
FIG. 11 shows the circuit diagram of the spectrogram computing unit.

According to a still further characteristic of the instant invention, the spectrogram processing unit 14 is provided according to the circuit-functional diagram of FIG. 11.

Two integrator-counters 111 and 112 receive as their input the sampled values of the deviations from the average value, coming from the subtractor node 60 along the connection 90, according to a sequence ensured by the four gates, 113, 113', 114 and 114'. These are enabled, one at a time, and after each other, by the sequencer 115, while an operator 116 changes the sign on the signal entering two of said gates, respectively 113 and 113', so that, in correspondence of the above said gates, the above said sampled values are subtracted from the contents of the counters.

At the end of a suitable sequence of said operations, the output from said counters 111 and 112 is sent to two dividers 117 which, by dividing the result by the number of the samples acquired and by the factor 0.45, normalize it to the same scale as of the sampled values of the deviations. Consequently, two values are obtained that are equal in the sinus and in the cosinus to the two Fourier coefficients.

The outputs of said values are then supplied as inputs to two operators 118 which square them, and the respective outputs are summed in the adder node 119, from which the square of the modulus of the two coefficients results then become available.

Said squared modulus is sent through the connection 54 and the interface 8 to the master 9 and is furthermore compared, by means of the comparator node 120, to a threshold value 121, which represents the limit of periodic irregularity, beyond which the circuit generates a stop signal through the connection 55.

The explanation of the operation of the disclosed circuit shown in FIG. 11 as a spectrum detector and the justifying of the degree of approximation achieved by such simple means, presupposes some simplifications and hypotheses which are characteristics of the system found.

The first simplification consists in hypothesizing that the harmonic content is constant throughout the yarn being examined so that carrying out the analysis sequentially, one frequency, i.e., one wavelength, at a time, is possible.

This approximation, even if it is not exact from a scientific viewpoint, is quite acceptable to define the quality of the yarn. It is not said, indeed, that a perfect spectrogram, built according to the presently in force standards, by examining in parallel the harmonic content of one single sample of 150 m of yarn, is more indicative of the quality of a large yarn batch than the spectrum detector of the present invention. The spectrogram of the present invention, which relates to defined yarn lengths for each wavelength, can be continuously repeated throughout the cone length; it is furthermore possible to average the results with a final representativeness which is hence much better than that of the standard.

A second simplification is that of determining the wavelengths to be examined not according to a homogeneous distribution and with constant pitches on logarithmic scale, but according to multiples of the sampling period, with the result of a not constant distribution of the degree of sensitivity astride the one wavelength and the other.

Also for the approximation caused by this assumption, what said for the previous one holds true.

By taking for granted what has been said about the discretization of the formulae for the computation of the Fourier coefficients for the % VC calculation, an improvement has been introduced over that was disclosed in FIG. 8 for the spectrogram.

In case of a spectrum, the modulus is indeed to be built, because the phase of the irregularities relative to the filter phase is not known, so that calculating both the $a_\lambda$'s and the $b_\lambda$'s of Fourier is necessary for deducing the modulus therefrom:

$$r = \sqrt{a_\lambda^2 + b_\lambda^2}$$

By using the digital filter of FIG. 8, the function "r" is variable, in the presence of a constant modulus, as a function of the phase, even if by not much.

Figure 12:
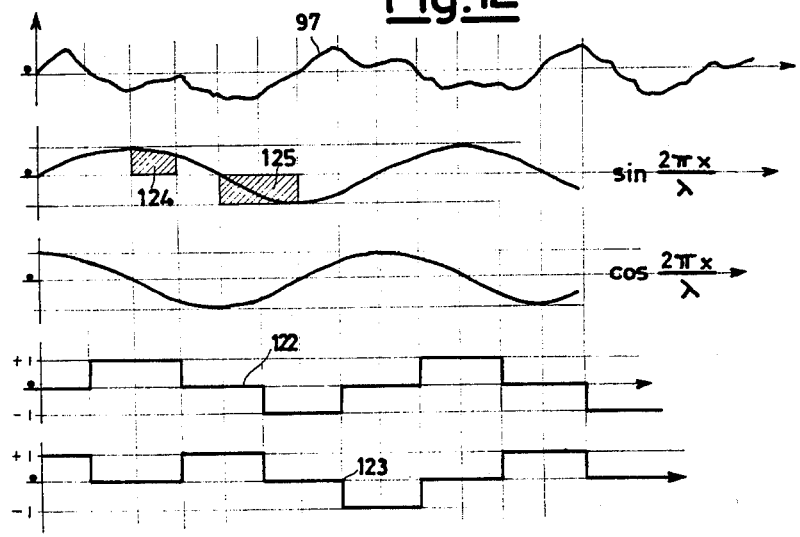
FIG. 12 shows a chart relating to the operation of the unit of FIG. 1.

The filter shown in FIG. 11, on the contrary, by carrying out the sum formation in the two counters 111 and 112 with the law of the signs, which is represented by the broken lines 122 and 123 of FIG. 12, reaches the result of obtaining the r function constant with varying signal phase, exactly equal to the actual modulus of the signal being examined.

In this filter, the wavelength $\lambda$ is equal to $4 \cdot Z \cdot m$, wherein Z is the number of the samples per each phase and m is the length corresponding to one sampling.

The wavelengths $\lambda$ of the filter are obtained by giving to Z values increasing according to such a table as to obtain, for example, with 64 values of Z, wavelengths ranging from 4 cm to 64 m.

According to a non-limitative characteristic of the present invention, a particular selection of the value of the length:

$$m = 2.5 \text{ mm}$$

allows the numerical coincidence to be obtained of the values of Z, number of the samplings per phase, with the wavelength in cm of the related filter.

The formulae for the calculation of the coefficients assume the form:

$$a_\lambda = \frac{2.22}{4 \cdot nZ} \sum_{1}^{4nZ} \pm e_D \quad \text{(III)}$$

$$b_\lambda = \frac{2.22}{4 \cdot nZ} \sum_{1}^{4nZ} \pm e_D \quad \text{(IV)}$$

$$r = \sqrt{a^2 + b^2} \quad \text{(V)}$$

For the selection of n, the law is valid of the selectivity increasing with increasing n; however, it cannot be increased up to a certain limit because the sequence of wavelengths $\lambda$ is discrete and it would correspond to noncollection of a signal when the actual wavelength of the defect is intermediate between two tabulated wavelengths.

For the practical requirements of the textile industry, n should be selected from the values close to and including 8 (e.g., 6–10).

The normalization factor $$\frac{2.22}{4 \cdot nZ}$$

is composed by a factor 2.22, the inverse of which is 0.45 (which is the ration of the area 124 to the area 125 of FIG. 12) and by the total number of the samplings 4.nZ.

The justification is omitted because it is elementary. It is elementary that this factor of normalization allows the Fourier coefficients to be obtained in the same scale as of the sampled values of the deviations.

A final characteristic of the instant invention is constituted by the device of maximum limit to the Fourier modulus accomplished as shown in diagram 11. This device allows an alternative to the interception of the Moire defects, relative to the diagram of units 12, useful for stopping Moire-type defects of a certain intensity during the processing of the spectrogram in case operation in parallel of the special units for the detection of the Moire defects 12 is not possible.

We claim:

1. An optical slub catcher for weaving unit of the open-end type comprising:
   (a) optical head means for measurement of yarn diameter that supplies an analog signal proportional to said yarn diameter, said analog signal being used to control production of yarn and to determine yarn characteristics;

(b) compensation means coupled to said optical head means for amplifying, demodulating, and normalizing said analog signal;

(c) an analog-digital converter coupled to said compensation means for converting said analog signal into a digital value;

(d) modulation means coupled to said optical head means for supplying said optical head means with a pulsating current;

(e) timer and sequences generator means coupled to said modulation means for driving said modulation means;

(f) central processing means for analyzing data and controlling the operations of said slub catcher connected to said modulation means and said timer and sequences generator means;

(g) presetting means for presetting a reference average yarn diameter connected to said central processing means;

(h) subtractor node means for calculating the error of a measured yarn diameter with said reference average yarn diameter connected to said central processing means;

(i) count control means for synchronizing the parts of said slub catcher connected to said central processing means; and (j) calculation means for calculating a unitary diameter of the yarn connected to said central processing means.

2. The optical slub catcher according to claim 1, wherein said optical head means comprises a "U" shaped block of material to permit double reflection of light rays, with a photoemitter and a photoreceiver being embedded within opposite ends of said "U" shaped block to keep equal the temperature of said photoemitter and photoreceiver.

3. The optical slub catcher according to claim 1, wherein said compensation means comprises:

(a) a current source amplifier circuit connected to said optical head means;

(b) chopper means, coupled to said current source amplifier circuit for sampling an amplified signal from said current source amplifier circuit, said amplified signal being supplied in positive feedback to said current source amplifier circuit;

(c) amplifier means coupled to said chopper means for eliminating variations caused by ambient light; and (d) an inverter amplifier coupled to said amplifier means.

4. The optical slub catcher according to claim 1, wherein said modulation means comprises:

(a) integrator circuit means functioning as a digital-analog converter, polarized at a prefixed voltage value, to which the intermediate point is connected of two gates, connected in series, submitted to a positive voltage, the value of which is the double of the above polarization voltage;

(b) a regulator of a feed current to said optical head coupled to said integrator circuit means; and (c) a set of resistors, polarizing an input level of said integrator circuit means, connected on one side to a summation node and connected at the opposite side to said central processing means.

5. The optical slub catcher according to claim 1, further comprising first detection means for Moire defects connected to said central processing means, wherein said first detection means for Moire defects comprises:

(a) a series of counters, to which sampled values are sent of the deviations from the average diameter calculated in said subtractor node;

(b) sequencer means controlling said series of counters such that said counters first sum a predetermined number of sequential sampled values, then subtracts an equal number of sequential values, to repeat the operations with a preset cadence corresponding to the length of yarn unwound during one revolution of a rotor and to repeat the sampling for a prefixed number of times, each of said series of counters being enabled to operate with a delay relative to the preceding counter, equal to the above stated predetermined number of sequential sampled values and having its output compared to two threshold values, said threshold values corresponding to a Moire forewarning or a stop due to Moire defects.

6. The optical slub catcher according to claim 1, further comprising second detection means for detecting non-Moire defects connected to said central processing means, wherein said second detection means for non-Moire defects includes a CV % irregularities detection means comprising:

(a) a squared counter, receiving a first input signal of the sampled values of the deviations from the average value;

(b) multiplier means sending to said squarer counter a second input signal, to be subtracted, representing multiplication of a preset value with a linear average of the sampled values of the deviations form the average diameter, performed on a determined yarn length; and (c) comparator means, receiving an output of said squarer counter representing the sum of the squares of the values along a predetermined length of yarn, the output of said squarer counter being compared to an acceptability threshold value, yielding a stop signal if there is an excess of CV % irregularity.

7. The optical slub catcher according to claim 1, further comprising spectrogram means for processing the spectrogram of irregularities connected to said central processing means, wherein said spectrogram means comprises:

(a) two integrator counters, to which sampled values of the deviation from the average diameter are delivered through four gates closed one at a time in a cyclic sequence, two of said gates being connected to a NOT element;

(b) two divider units, each of said divider units coupled to one of said counter integrators, for dividing by a constant value, proportional to the total number of the detected sampled values;

(c) two squarer operator means, each of said squared means coupled to one of said divider units, for squaring ad output of each of said divider units, with the outputs of said squarer unit being summed to each other and the sum value being delivered to a spectrogram process unit comparator, wherein the sum value is compared to a prefixed limit value, to stop the weaving operation in case of excessive irregularity.

8. The optical slub catcher according to claim 1, further comprising correction means for automatic correction of a zero connected to said central processing means, wherein said correction means comprises:

(a) a counter integrator, to which sampled values of the deviation from the average diameter are delivered, said counter integrator being coupled to said count control means;

(b) correction comparator means, coupled to said counter integrator, in which the summation of all the said sampled values, relating to a prefixed lenght, is compared: on one side to a limit value, said correction comparator means being connected to a gate connecting said counter integrator with a multiplier, said multiplier being connected to said calculation means;

(c) a sign discriminator coupled to said multiplier; and (d) a digital-analog converter coupled to said sign discriminator.

* * * * *